United States Patent [19]

Arai et al.

[11] Patent Number: 4,950,322
[45] Date of Patent: Aug. 21, 1990

[54] CYCLOHEXANE HERBICIDES FOR GRAMINEOUS CROPS

[75] Inventors: Kenji Arai, Takarazuka; Kouichi Morita, Toyonaka; Nobuaki Mito, Takarazuka; Naonori Hirata, Sakai, all of Japan

[73] Assignee: Sumitomo Chemical Company, Limited, Osaka, Japan

[21] Appl. No.: 104,932

[22] Filed: Oct. 6, 1987

[30] Foreign Application Priority Data

Dec. 19, 1986 [JP] Japan .................... 61-304827

[51] Int. Cl.$^5$ .......................... A01N 31/04
[52] U.S. Cl. ................................ 71/98
[58] Field of Search ......................... 71/98

[56] References Cited

U.S. PATENT DOCUMENTS

| | | | |
|---|---|---|---|
| 4,249,937 | 2/1981 | Iwataki et al. | 71/98 |
| 4,440,566 | 4/1984 | Luo | 71/98 |
| 4,555,263 | 11/1985 | Serban et al. | 71/98 |
| 4,626,276 | 12/1986 | Luo | 71/98 |
| 4,728,357 | 3/1988 | Becker et al. | 71/98 |

FOREIGN PATENT DOCUMENTS

| | | | |
|---|---|---|---|
| 0085529 | 8/1983 | European Pat. Off. | 71/98 |
| 3230087 | 2/1984 | Fed. Rep. of Germany | 71/98 |
| 54-46749 | 4/1979 | Japan | 71/98 |
| 54-115349 | 9/1979 | Japan | 71/98 |
| 55-89203 | 7/1980 | Japan | 71/98 |

*Primary Examiner*—Glennon H. Hollrah
*Attorney, Agent, or Firm*—Stevens, Davis, Miller & Mosher

[57] ABSTRACT

A herbicidal composition for gramineous crops which comprises as an active ingredient a herbicidally effective amount of the compound represented by the general formula,

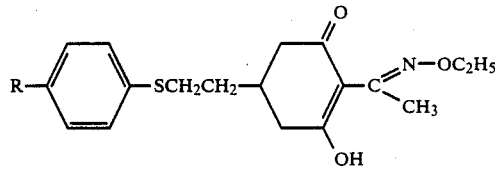

wherein R represents a chlorine atom, a methyl group or a methoxy group.

4 Claims, No Drawings

CYCLOHEXANE HERBICIDES FOR GRAMINEOUS CROPS

The present invention relates to a herbicide for gramineous crops containing as an active ingredient a cyclohexane derivative represented by the general formula (I),

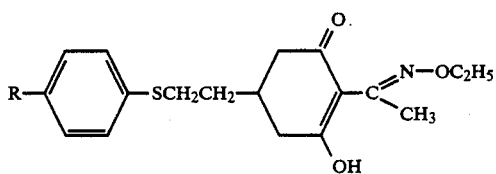

wherein R represents a chlorine atom, a methyl group or a methoxy group.

Hitherto, it is described in U.S. Pat. No. 4,249,937 that a certain kind of cyclohexane derivatives can be used as an active ingredient for herbicides.

The compounds described in said patent are generally effective in the control of grassy weeds and hardly injure broadleaf crops, but because of their poor selectivity between gramineous crops and grassy weeds, they may not always be said to be satisfactory as a herbicide for gramineous crops.

In view of the situation like this, the present inventors made an extensive study and as a result, found a compound having excellent herbicidal activity against grassy and broadleaf weeds, particularly grassy weeds at low dosage rates and yet showing no phytotoxicity to gramineous crops. The present inventors thus attained to the present invention.

The cyclohexane derivatives represented by the general formula (I), in foliage treatment and soil treatment in the field of gramineous crops, have excellent herbicidal activity at low dosage rates against various weeds in question, for example grassy weeds such as Japanese millet (*Echinochloa frumentacea*), barnyardgrass (*Echinochloa crus-galli*), green foxtail (*Setaria viridis*), large crabgrass (*Digitaria sanguinalis*), annual bluegrass (*Poa annua*), blackgrass (*Alopeucrus myosuroides*), oat (*Avena sativa*), wild oat (*Avena fatua*), johnsongrass (*Sorghum halepense*), downy brome (*Bromus tectorum*), etc. as well as broadleaf weeds such as common purslane (*Portulaca oleracea*), redroot pigweed (*Amaranthus retroflexus*), radish (*Raphanus sativus*), black nightshade (*Solanum nigrum*), persian speedwell (*Veronica persica*), etc. Besides, their phytotoxicity to gramineous crops such as corn, rice, etc. is not such a one as to cause a problem.

Also, the cyclohexane derivatives (I), in treatment under flooded condition in paddy field, have a herbicidal activity at low dosage rates against various weeds in question, for example grassy weeds such as barnyardgrass (*Echinochloa oryzicola*), etc. and broadleaf weeds such as common falsepimpernel (*Lindernia procumbens*), long stemmed waterwort (*Elatine triandra*), etc., and yet, their phytotoxicity to rice is not such a one as to cause a problem.

The cyclohexane derivatives (I) are preferred particularly in foliage treatment in corn fields.

When the cyclohexane derivatives (I) are used as an active ingredient for the present herbicides, they are generally formulated into emulsifiable concentrates, wettable powders, suspension formulations, granules, etc. by mixing with solid carriers, liquid carriers, surface active agents and other auxiliaries for formulation.

These preparations contain as an active ingredient from 0.1 to 90% by weight, preferably from 0.2 to 80% by weight of the cyclohexane derivatives (I).

The solid carriers include fine powders or granules of kaolin clay, attapulgite clay, bentonite, terra abla, pyrophyllite, talc, diatomaceous earth, calcite, walnut powder, urea, ammonium sulfate, synthetic hydrated silicon dioxide, etc. The liquid carriers include aromatic hydrocarbons (e.g. xylene, methylnaphthalene), alcohols (e.g. isopropanol, ethylene glycol, cellosolve), ketones (e.g. acetone, cyclohexanone, isophorone), vegetable oils (e.g. soybean oil, cotton seed oil), dimethyl sulfoxide, N,N-dimethylformamide, acetonitrile, water, etc.

The surface active agents used for emulsification, dispersion, wetting, etc. include anionic surface active agents such as the salt of alkyl sulfates, alkylsulfonates, alkylarylsulfonates, dialkyl sulfosuccinates, the salt of polyoxyethylene alkylaryl ether phosphoric acid ester, etc., and nonionic surface active agents such as polyoxyethylene alkyl ether, polyoxyethylene alkylaryl ether, polyoxyethylene polyoxypropylene block copolymers, sorbitan fatty acid esters, polyoxyethylene sorbitan fatty acid esters, etc.

The auxiliaries for formulation include lignosulfonates, alginates, polyvinyl alcohol, gum arabic, CMC (carboxymethyl cellulose), PAP (isopropyl acid phosphate), etc.

Generally, the cyclohexane derivatives (I) are formulated and used in soil treatment, foliage treatment or treatment under flooded condition before or after the emergence of weeds. The soil treatment includes soil surface treatment, soil incorporation treatment, etc., and the foliage treatment includes, in addition to the treatment of plants over the top, directed treatment wherein herbicides are applied to weeds only so as not to attach to crops.

Also, an increase in herbicidal activity can be expected by using the present herbicides in mixture with other herbicides. In addition, the present herbicides can be used in mixture with insecticides, acaricides, nematocides, fungicides, plant growth regulators, fertilizers, soil improvers, etc.

Further, the cyclohexane derivatives (I) can be used as an active ingredient for paddy fields, plow fields, orchards, pastures, turfs, forests or non-crop lands.

When the cyclohexane derivatives (I) are used as an active ingredient for the present herbicides, their dosage rate varies with weather conditions, preparation forms, when, how and where the treatments are applied, weeds to control, gramineous crops to protect, etc. Generally, however, the dosage rate is from 0.05 to 10 g/are, preferably from 0.1 to 2 g/are, but even less than 1 g is sufficient. In the case of emulsifiable concentrates, wettable powders, suspension formulations, etc., their prescribed amount is generally diluted with water of from 1 to 10 liters/are (if necessary, auxiliaries such as spreading agents are added). Granules, etc. are generally used as such without dilution.

The spreading agents include, in addition to the foregoing surface active agents, polyoxyethylene resin acid (ester), lignosulfonates, abietates, dinaphthylmethanedisulfonates, paraffin, etc.

The cyclohexane derivatives (I) can be produced by the following method. That is, the cyclohexane derivatives represented by the general formula (I) can be produced by reacting an acetylcyclohexane derivative represented by the formula,

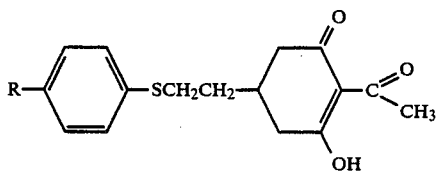

wherein R represents the same meaning as described above, with ethoxyamine represented by the formula, $$NH_2=OC_2H_5 \quad (III)$$

or its inorganic acid salt.

This reaction is generally carried out with or without a solvent, and as need arises, in the presence of a base. The range of the reaction temperature is from 0° to 100° C., and that of the reaction time is from 1 to 24 hours. As to the amount of the reagents used in the reaction, the amount of the compound (III) or its inorganic acid salt is from 1 to 1.5 equivalents based on 1 equivalent of the compound (II), and that of the base is from 1 to 1.5 equivalents based on the same.

The solvent includes aliphatic hydrocarbons (e.g. hexane, heptane, ligroin, petroleum ether), aromatic hydrocarbons (e.g. benzene, toluene, xylene), halogenated hydrocarbons (e.g. chloroform, carbon tetrachloride, dichloroethane, chlorobenzene, dichlorobenzene), ethers (e.g. diethyl ether, diisopropyl ether, dioxane, tetrahydrofuran, diethylene glycol dimethyl ether), alcohols (e.g. methanol, ethanol, isopropanol, tert-butanol, octanol, cyclohexanol, methyl cellosolve, diethylene glycol, glycerin), esters (e.g. ethyl formate, ethyl acetate, butyl acetate, diethyl carbonate), nitro compounds (e.g. nitroethane, nitrobenzene), nitriles (e.g. acetonitrile, isobutyronitrile), tertiary amines (e.g. pyridine, triethylamine, N,N-diethylaniline, tributylamine, N-methylmorpholine), acid amides (e.g. formamide, N,N-dimethylformamide, acetamide), sulfur compounds (e.g. dimethyl sulfoxide, sulfolane), water and mixtures thereof.

The base includes organic bases (e.g. pyridine, triethylamine, N,N-dimethylaniline), inorganic bases (e.g. sodium hydroxide, potassium hydroxide, sodium carbonate, potassium carbonate, sodium hydride), alkali metal alkoxides (e.g. sodium methoxide, sodium ethoxide), etc.

The inorganic acid salt of the compound (III) includes hydrochloride, hydrobromide, sulfate, etc.

After completion of the reaction, the desired cyclohexane derivatives (I) can be obtained by pouring the reaction solution into water, acidifying the resulting aqueous solution, and subjecting the solution to the usual after-treatment such as extraction with organic solvents, concentration, etc. and if necessary, purifying by operations such as chromatography, recrystallization, etc.

The cyclohexane derivatives (I) are considered to have the following tautomeric structures:

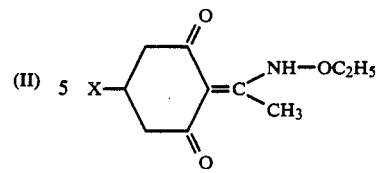

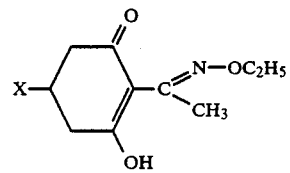

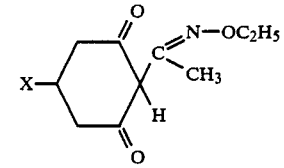

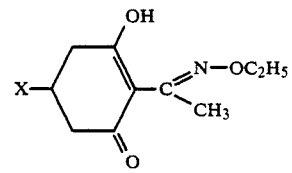

[In the above formulae,

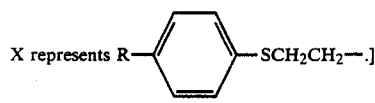

X represents R—⟨phenyl⟩—SCH₂CH₂—.]

Next, production of the cyclohexane derivatives (I) will be illustrated with reference to the following reference examples.

Reference example 1

0.8 Gram of 2-acetyl-5-[2-(4-chlorophenylthio)ethyl]-cyclohexane-1,3-dione was dissolved in 80 ml of ethanol, and after adding 0.31 g of ethoxyamine hydrochloride and 0.32 g of triethylamine, the resulting solution was stirred overnight at room temperature. The reaction solution was poured into water, acidified with dilute hydrochloric acid and extracted with chloroform. After removing chloroform, the product obtained was purified by thin layer chromatography (developing solvent, hexane:ethyl acetate=3:1) to obtain 0.43 g of 2-(1-ethoxyaminoethylidene)-5-[2-(4-chlorophenylthio)ethyl]cyclohexane-1,3-dione [Compound (1)].

$n_D^{24}$ 1.4852

Nuclear magnetic resonance spectrum (CDCl₃): δ (ppm) 15-14 (1H, br), 7.32 (4H, s), 4.09 (2H, q), 2.90 (2H, t), 2.33 (3H, s), 3.0-1.5 (7H, m), 1.28 (3H, t).

Reference example 2

0.6 Gram of 2-acetyl-5-[2-(4-methylphenylthio)ethyl]cyclohexane-1,3-dione was dissolved in 60 ml of ethanol, and after adding 0.25 g of ethoxyamine hydrochloride and 0.26 g of triethylamine, the resulting solution was stirred overnight at room temperature. The reaction solution was poured into water, acidified with dilute hydrochloric acid and extracted with chloroform. After removing chloroform, the product obtained was purified by thin layer chromatography (developing solvent, hexane:ethyl acetate=3:1) to obtain 0.4 g of 2-(1-ethoxyaminoethylidene)-5-[2-(4-methylphenylthio)ethyl]cyclohexane-1,3-dione [Compound (2)].

$n_D > 1.5808$

Nuclear magnetic resonance spectrum (CDCl$_{03}$): δ (ppm) 15–14 (1H, br), 7.19 (4H, ABq), 4.09 (2H, q), 2.91 (2H, t), 2.35 (3H, s), 2.29 (3H, s), 2.8–1.5 (7H, m), 1.29 (3H, t).

Reference example 3

0.7 Gram of 2-acetyl-5-[2-(4-methoxyphenylthio)ethyl]cyclohexane-1,3-dione was dissolved in 70 ml of ethanol, and after adding 0.27 g of ethoxyamine hydrochloride and 0.28 g of triethylamine, the resulting solution was stirred overnight at room temperature.

The reaction solution was poured into water, acidified with dilute hydrochloric acid and extracted with chloroform. After removing chloroform, the product obtained was purified by thin layer chromatography (developing solvent, hexane:ethyl acetate=3:1) to obtain 0.51 g of 2-(1-ethoxyaminoethylidene)-5-[2-(4-methoxyphenylthio)ethyl]cyclohexane-1,3-dione [Compound (3)].

$n_D^{23}$ 1.5738

Nuclear magnetic resonance spectrum (CDCl$_3$): δ (ppm) 15–14 (1H, br), 7.44 (4H, ABq), 4.47 (2H, q), 4.13 (3H, s), 3.22 (2H, t), 2.73 (3H, s), 3.0–1.5 (7H, m), 1.68 (3H, t).

Next, formulation examples will be shown. Parts in the examples are by weight.

Formulation example 1

Fifty parts of the compound (1), 3 parts of calcium lignosulfonate, 2 parts of sodium lauryl sulfate and 45 parts of synthetic hydrated silicon dioxide are well pulverized and mixed together to obtain a wettable powder.

Formulation example 2

Ten parts of each of the compounds (1), (2) and (3), 14 parts of polyoxyethylene styrylphenyl ether, 6 parts of calcium dodecylbenzenesulfonate, 30 parts of xylene and 40 parts of cyclohexanone are well mixed to obtain an emulsifiable concentrate.

Formulation example 3

Two parts of the compound (3), 1 part of synthetic hydrated silicon dioxide, 2 parts of calcium lignosulfonate, 30 parts of bentonite and 65 parts of kaolin clay are well pulverized and mixed together, well kneaded with water, granulated and dried to obtain a granule.

Formulation example 4

Twenty-five parts of the compound (2), 3 parts of polyoxyethylene sorbitan monooleate, 3 parts of CMC and 69 parts of water are mixed and wet-pulverized until the particle size is reduced to 5 microns or less to obtain a suspension formulation.

Next, the usefulness of the cyclohexane derivatives (I) as an active ingredient for the present herbicides will be illustrated with reference to the following test examples. In the test examples, a compound used as a control is shown by Compound symbol in Table 1.

TABLE 1

| Compound symbol | Structural formula | Remark |
|---|---|---|
| A | CH$_3$—C$_6$H$_4$—SCH$_2$CH$_2$—[cyclohexenone with =NOCH$_2$CH=CH$_2$, C$_3$H$_7$, OH substituents] | Compound described in U.S. Pat. No. 4249937. |

The herbicidal activity and phytotoxicity were evaluated in six stages, 0, 1, 2, 3, 4, 5, according to the states of the emergence and growth of test plants (weeds and crops) at the time of examination. A stage "0" means there being little or no difference in the states between the treated test plants and untreated ones; a stage "5" means the complete death of test plants or complete inhibition of the emergence or growth thereof; and the states between "0" and "5" are divided into four stages, 1, 2, 3 and 4.

Test example 1 Foliage treatment test in plow field

Plow-field soil was filled in a vat (area, 33×23 cm$^2$; depth, 11 cm), and the seeds of corn, barnyardgrass, large crabgrass, johnsongrass, green foxtail and oat were sowed and cultivated for 18 days. Thereafter, the prescribed amount of the emulsifiable concentrates of the test compounds prepared according to Formulation example 2 was diluted with water of an amount corresponding to 10 liters/are, and uniformly applied to the entire foliage of the test plants over the top by means of a small-sized sprayer. The state of growth of the weeds and crops at that time varied with the kind thereof, but they were in a 1 to 4-leaf stage and from 2 to 12 cm in height. Twenty days after treatment, the herbicidal activity was examined. The results are shown in Table 3. These tests were carried out in a greenhouse through the entire period of test.

TABLE 2

| Test compound | Dosage rate of active ingredient (g/a) | Herbicidal activity | | | | | |
|---|---|---|---|---|---|---|---|
| | | Corn | Barnyard-grass | Large crabgrass | Johnson-grass | Green foxtail | Oat |
| (1) | 0.63 | 1 | 5 | 4 | — | 4 | 4 |
| (2) | 0.63 | 1 | 4 | 3 | — | 3 | — |
| (3) | 0.63 | 2 | 5 | 3 | 4 | 3 | 4 |

TABLE 2-continued

| Test compound | Dosage rate of active ingredient (g/a) | Herbicidal activity | | | | | |
|---|---|---|---|---|---|---|---|
| | | Corn | Barnyard-grass | Large crabgrass | Johnson-grass | Green foxtail | Oat |
| A | 0.63 | 3 | 5 | 2 | 1 | 4 | 3 |

Test example 2 Foliage treatment test in plow field

Plow-field soil was filled in a vat (area, 15×10 cm²; depth, 7 cm), and the seeds of corn, barnyardgrass, green foxtail and large crabgrass were sowed and cultivated for 14 days. Thereafter, the prescribed amount of the emulsifiable concentrates of the test compounds prepared according to Formulation example 2 was diluted with water of an amount corresponding to 10 liters/are, and uniformly applied to the entire foliage of the test plants over the top by means of a small-sized sprayer. The state of growth of the weeds and crops at that time varied with the kind thereof, but they were in a 1 to 4-leaf stage and from 2 to 42 cm in height. Fifteen days after treatment, the herbicidal activity was examined. The results are shown in Table 3. These tests were carried out in a greenhouse through the entire period of test.

TABLE 3

| Test compound | Dosage rate of active ingredient (g/a) | Herbicidal activity | | | |
|---|---|---|---|---|---|
| | | Corn | Barnyard-grass | Green Foxtail | Large crabgrass |
| (1) | 1.25 | 2 | 5 | 5 | 5 |
| | 0.5 | 0 | 5 | 4 | 4 |
| (2) | 1.25 | 2 | 5 | 5 | 5 |
| | 0.5 | 0 | 5 | — | 4 |
| (3) | 1.25 | 2 | 5 | 5 | 5 |
| | 0.5 | 0 | 4 | — | — |
| A | 1.25 | 4 | 5 | 4 | 3 |
| | 0.5 | 1 | 3 | 3 | 2 |

Test example 3 Soil treatment test in plow field

Plow-field soil was filled in a vat (area, 33×23 cm²; depth, 11 cm), and the seeds of corn, barnyardgrass, large crabgrass, green foxtail and fall panicum were sowed and covered from 1 to 2 cm deep with the soil. The prescribed amount of the emulsifiable concentrates of the test compounds prepared according to Formulation example 2 was diluted with water of an amount corresponding to 10 liters/are, and applied to the soil surface by means of a small-sized sprayer. After treatment, the test plants were cultivated for 20 days in a greenhouse to examine the herbicidal activity. The results are shown in Table 4.

TABLE 4

| Test compound | Dosage rate of active ingredient (g/a) | Herbicidal activity | | | | |
|---|---|---|---|---|---|---|
| | | Corn | Barnyard-grass | Large crabgrass | Green foxtail | Fall panicum |
| 1 | 2.0 | 0 | 4 | 4 | 5 | 4 |
| 2 | 2.0 | 0 | 4 | 4 | 5 | — |

Test example 4 Treatment test under flooded condition in paddy field

Paddy-field soil was filled in 1/5000 ares Wagner's pots, and the seeds of barnyardgrass were incorporated from 1 to 2 cm deep in the soil. After creating the state of paddy field by flooding, rice plants in a 3-leaf stage were transplanted and cultivated in a greenhouse. After 4 days, the prescribed amount of the emulsifiable concentrates of the test compounds prepared according to Formulation example 2 was diluted with 10 ml of water and applied to the water surface, and the depth of water was made 4 cm. After treatment, the test plants were cultivated for 20 days in a greenhouse to examine the herbicidal activity and phytotoxicity. The results are shown in Table 5. In this test, water leakage corresponding to a water level of 3 cm/day was carried out for 2 days from the day subsequent to the treatment.

TABLE 5

| Test compound | Dosage rate of active ingredient (g/a) | Phytotoxicity Rice | Herbicidal activity Barnyard-grass |
|---|---|---|---|
| 1 | 1.25 | 1 | 5 |
| | 0.32 | 0 | — |
| 2 | 1.25 | 1 | 5 |
| | 0.32 | 0 | 5 |

What is claimed is:

1. A method for controlling undesired gramineous weeds in a field of corn which comprises applying 0.05-2 g/are of the compound represented by the formula,

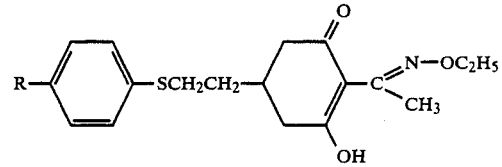

wherein R represents a chlorine atom, a methyl group or a methyoxy group, and an inert carrier and/or diluent to the field of gramineous crops.

2. A method according to claim 1, which comprises applying 0.1-2 g/are of said compound to the field of corn.

3. A method according to claim 1, which comprises diluting an emulsifiable concentrate comprising 0.1-90 parts by weight of said compound and 10-99.9 parts by weight of an inert carrier and/or diluent with water and applying 1-10 liters/are of the resulting emulsion to the field of corn.

4. A method according to claim 1, which comprises diluting an emulsifiable concentrate comprising 0.2-80 parts by weight of said compound and 20-99.8 parts by weight of an inert carrier and/or diluent with water and applying 1-10 liters/are of the resulting emulsion to the field of corn.

* * * * *